US00PP34166P3

(12) United States Plant Patent
Smith

(10) Patent No.: US PP34,166 P3
(45) Date of Patent: Apr. 26, 2022

(54) MANDARIN TREE NAMED '11C017R'

(50) Latin Name: *Citrus reticulata*
Varietal Denomination: 11C017R

(71) Applicant: State of Queensland Through the Department of Agriculture and Fisheries, Brisbane (AU)

(72) Inventor: Malcolm W. Smith, Brisbane (AU)

(73) Assignee: State of Queensland Through the Department of Agriculture and Fisheries, Brisbane (AU)

( * ) Notice: Subject to any disclaimer, the term of this patent is extended or adjusted under 35 U.S.C. 154(b) by 0 days.

(21) Appl. No.: 17/167,630

(22) Filed: Feb. 4, 2021

(65) Prior Publication Data

US 2021/0251118 P1 Aug. 12, 2021

Related U.S. Application Data

(60) Provisional application No. 62/971,560, filed on Feb. 7, 2020.

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202
CPC ..... A01H 6/785; A01H 5/08
See application file for complete search history.

*Primary Examiner* — Keith O. Robinson
(74) *Attorney, Agent, or Firm* — Morrison & Foerster LLP

(57) ABSTRACT

A new and distinct variety of mandarin tree named '11C017R', particularly selected for non-acidic flavour profiles and distinguished by the smooth skin texture, cleanness of peeling and high Brix levels, is disclosed.

3 Drawing Sheets

Latin name:

Botanical classification: *Citrus reticulata.*

Varietal denomination: The varietal denomination of the claimed variety of mandarin tree is '11C017R'.

BACKGROUND OF THE INVENTION

Mandarin is an important and valuable commercial fruit crop. Accordingly, there is a need for new varieties of mandarin trees. In particular, there is a need for improved varieties of mandarin trees for fresh fruit consumption in markets with a preference for non-acidic flavor profiles.

SUMMARY OF THE INVENTION

In order to meet these needs, the present invention is directed to an improved variety of mandarin tree. In particular, the invention relates to a new and distinct variety of mandarin tree (*Citrus reticulata*), which has been denominated as '11C017R'.

The initial step in the invention involved selection from a breeding population of approximately 6,000 hybrids between the female parent 'Ellendale' (unpatented) and the male parent 'Murcott' (unpatented), which was made in 2001. A single plant from this hybrid population (progenitor plant) was selected and was subject to two rounds of mutation breeding (2011, 1,385 plants; 2013, 387 plants) using a cobalt 60 gamma cell to create a stable mutation that maintained high fruit quality and production, and that had low seed numbers per fruit. '11C017R' was asexually propagated onto 'Troyer' (unpatented) rootstock and 54 trees were planted at two sites in central Queensland in 2016. Observation and testing of the 54 trees planted at two sites in central Queensland confirmed the stable retention of distinct characteristics of '11C017R'.

'11C017R' trees produce heavy crops of medium to large fruit that mature in the middle of the mandarin harvest season (end of May in Queensland, Australia). The fruit are firm and yet still relatively easy to peel, and the skin texture is smooth and without a prominent neck at the stem end. The fruit peel cleanly and have low seed numbers. High Brix levels are balanced with moderate acidity giving a sweet flavor well suited to Asian markets that prefer non-acidic fruit. Simulation experiments indicate that this invention is suitable for long-distance shipping while retaining its distinct mandarin characteristics.

'11C017R' was particularly selected for its non-acidic flavour profiles.

BRIEF DESCRIPTION OF THE DRAWINGS

Mandarin tree variety '11C017R' is shown in the accompanying photographs, illustrating typical fruit external and internal appearance, uniformity and tree productivity. The illustrated trees and fruit were grown under subtropical conditions in central Queensland, Australia and colors are as true as can be captured photographically. The photographs are of plants that are three years old.

DETAILED BOTANICAL DESCRIPTION

Figure 1:
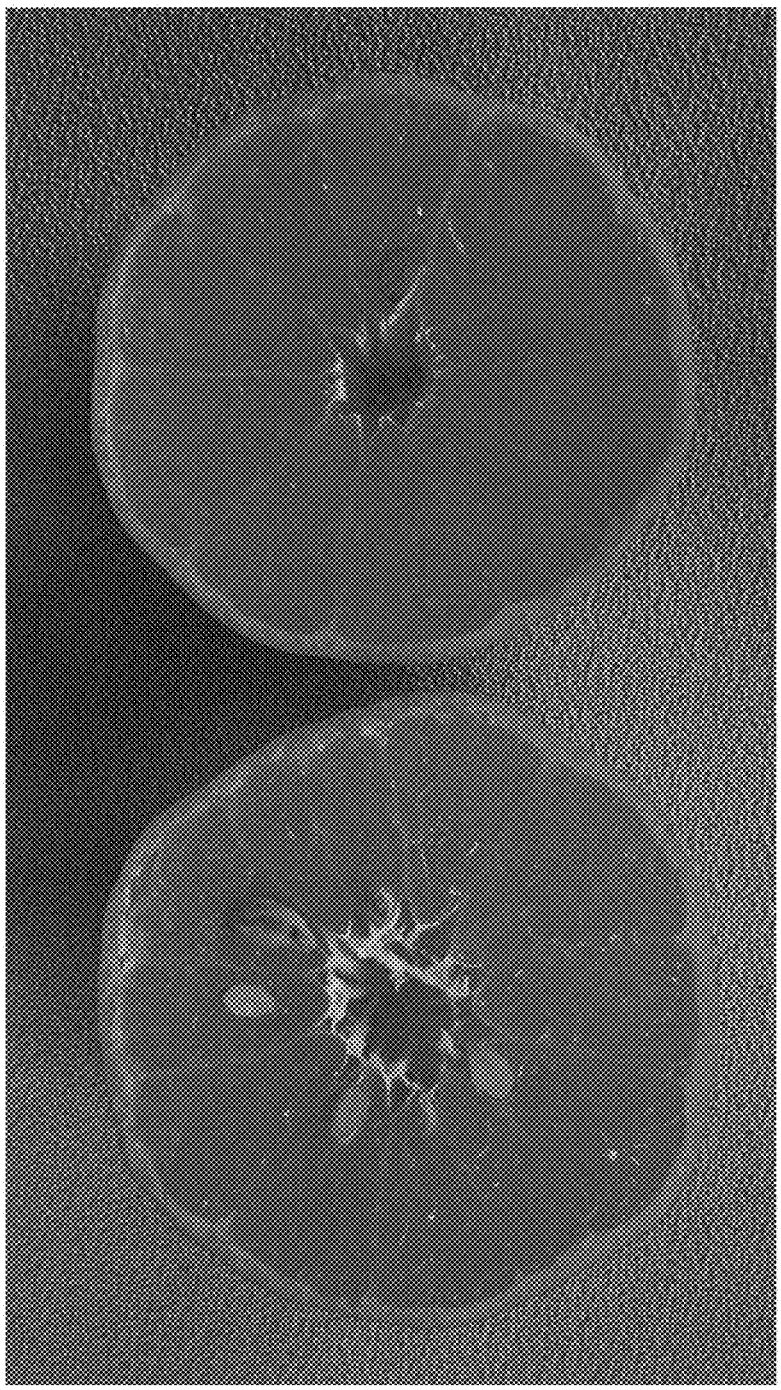
FIG. 1 shows fruit cross-section of '11C017R' (right panel) compared to its progenitor from the initial hybrid population with higher seed numbers (left panel) used during the two rounds of mutation breeding that gave rise to '11C017R'.
Figure 2:
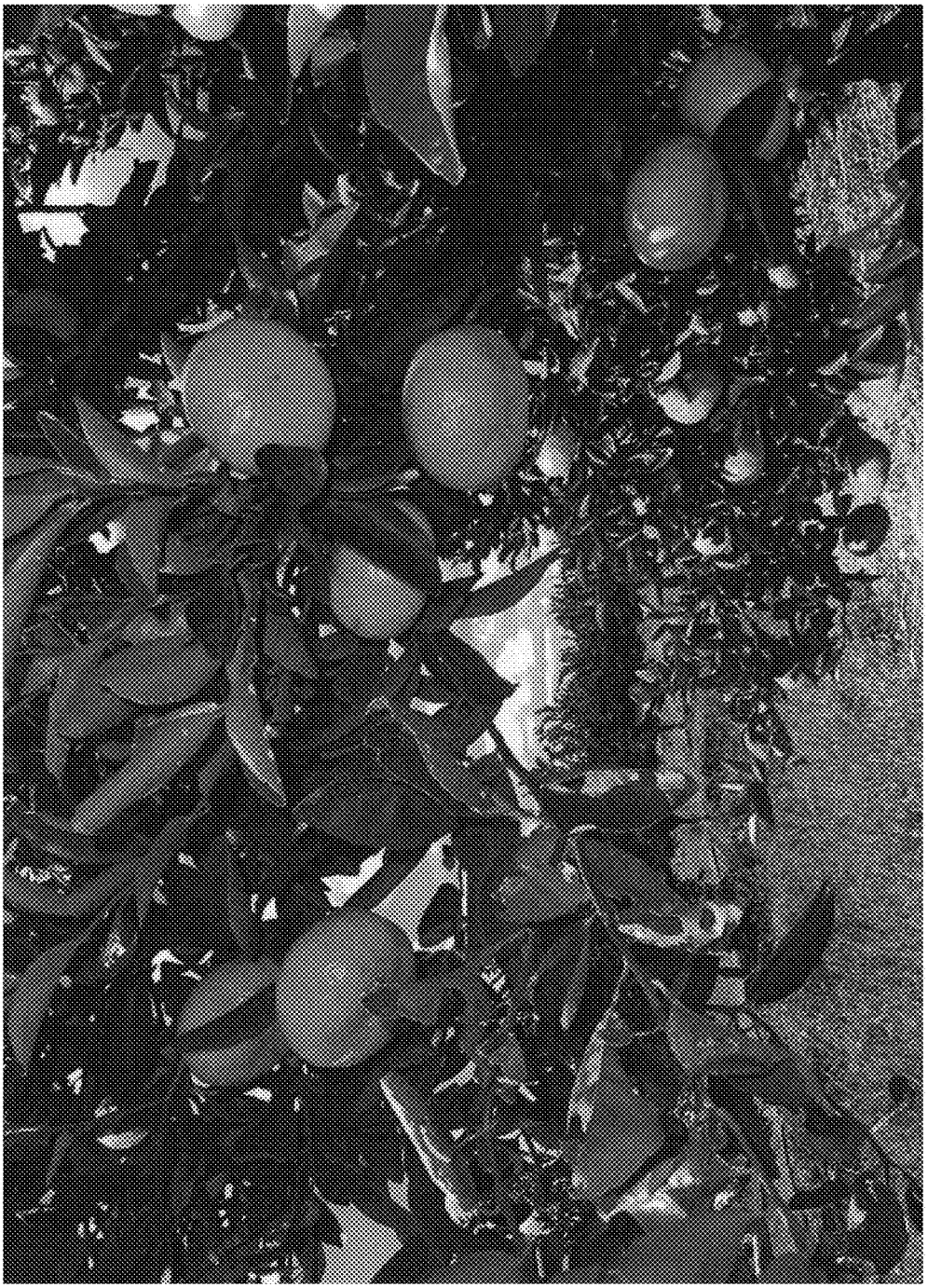
FIG. 2 shows whole fruit on the branch of '11C017R' along with typical leaf morphology.
Figure 3:
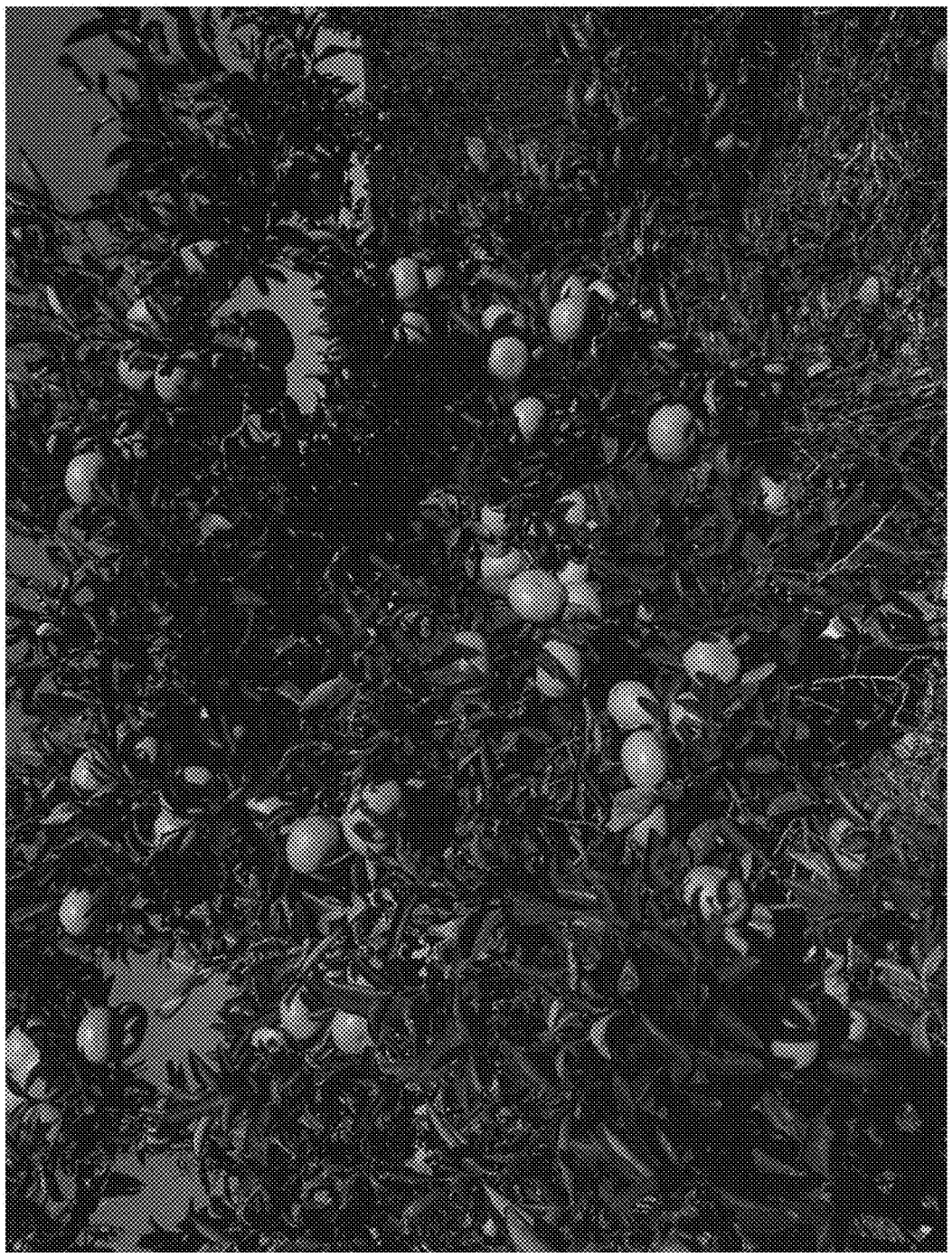
FIG. 3 shows a tree of '11C017R' with typical fruit and crop load.

The following descriptions set forth the distinctive characteristics of '11C017R'. Unless where otherwise noted, the data that define these characteristics are based on observations taken from '11C017R' plants that were three years old, grown on 'Troyer' (unpatented) rootstock in a subtropical environment at Gayndah, Australia. Color designations, color descriptions, and other phenotypical descriptions may deviate from the stated values and descriptions depending upon variation in environmental, seasonal, climatic and cultural conditions. '11C017R' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rutaceae.

*Botanical.—Citrus reticulata.*

*Common name*.—Mandarin.

*Variety name*.—'11C017R'.

Tree:

*Ploidy*.—Diploid.

*Size*.—Trees have a medium to large stature.

*Height*.—3.8 m.

*Spread*.—3.7 m.

*Vigor*.—Trees grow vigorously when young but early and heavy cropping helps to restrain subsequent vigor.

*Growth habit*.—Elliptic to oblong.

*Density*.—Canopy is light to medium in density resulting from long branches with sometimes low crotch angles.

*Bearing*.—Very productive from an early age with no evidence of alternate bearing.

Trunk:

*Trunk diameter*.—21.5 cm at 30 cm above graft.

*Trunk texture*.—Finely raised.

Branches:

*Crotch angle*.—Major branches at 45-50-degree crotch angle.

*Branch length*.—1.3 to 1.7 m.

*Branch width*.—9 to 12 cm.

*Branch texture*.—Smooth becoming finely raised on older branches.

*Branch color*.—RHS N200C (Grey).

*Thorns*.—Occasional on some branches and large, up to 7 cm.

Leaves:

*Size* (*lamina average*).—Length: 67 mm. Width: 40 mm. L/W ratio: 1.7.

*Arrangement*.—Alternate.

*Type*.—Simple.

*Shape*.—Obovate.

*Blade margin*.—Crenate.

*Apex shape*.—Obtuse, emarginated at tip.

*Petiole length*.—10 mm.

*Petiole diameter*.—2 mm.

*Petiole wings*.—Rudimentary <1 mm width.

*Petiole attachment*.—Articulate, brevipetiolate.

Flowers:

*Type*.—Hermaphroditic.

*Blooming period*.—Commencing ~25th August with full bloom ~24th September in Queensland, Australia.

*Flower petals*.—Number: 5. Color: RHS 155B (white). Length: 11 mm. Width: 4 mm. Calyx: Small. Texture: Smooth. Apex: Distinctly rounded (obtuse). Margin: Entire and imbricate. Base: Truncate.

*Fragrance*.—Typical of mandarin.

*Reproductive organs*.—Fertility: Self-fertile. Pollen amount: Moderately abundant. Pollen fertility: Low (assessed via aceto-carmine staining). Pollen color: RHS 22A (Dark orange yellow).

Fruit:

*Axial diameter*.—85 mm.

*Apical diameter*.—55 mm.

*Length*.—43 mm.

*Weight*.—210 g.

*General shape in profile*.—Obloid.

*Shape in transverse section*.—Somewhat angular.

*Shape of fruit base*.—Truncate, occasionally with wrinkles.

*Shape of fruit apex*.—Truncate.

*Position of the broadest part of the fruit*.—At middle.

*Depression at the stalk end*.—Absent.

*Depression at the distal end*.—Absent.

*Neck*.—Absent.

*Fruit surface texture*.—Smooth.

*Fruit surface color*.—RHS 26A (Orange-yellow).

*Fruit surface glossiness*.—Strong.

*Adherence of mesocarp to endocarp*.—Weak and peels away clean.

*Navel*.—Absent.

*Areola*.—Generally absent but occasionally grooved.

*Rind thickness*.—3.3 mm.

*Segment number*.—10-12.

*Harvest window*.—Mid-season: Late-May to Early-July (southern hemisphere subtropics).

*Fruit flesh color*.—RHS 25A (Orange).

*Juice soluble solid*.—12.6° Brix (mid-June).

*Juice acidity*.—0.48% citric acid equivalent (mid-June).

*Parthenocarpy*.—Present but weak.

*Seeds*.—0-5 per fruit.

*Seed type*.—Monoembryonic.

*Alternaria brown spot reaction*.—Susceptible.

Comparison of '11C017R' with its Female Parent 'Ellendale', Male Parent 'Murcott', and Reference Mandarin Variety 'Afourer':

| Character | '11C017R' | 'Ellendale' | 'Murcott' | 'Afourer' |
|---|---|---|---|---|
| Tree growth habit | elliptic to oblong | elliptic | obovate | elliptic to obovate |
| Alternaria Brown Spot disease | susceptible | resistant | susceptible | resistant |
| Pollen fertility | low | high | moderate | high |
| Seeds per fruit in mixed variety plantings | 0-5 | 20-30 | 20-30 | 15-25 |
| Presence of navel | absent | occasional | absent or very rare | absent or rare |
| Seed type | mono-embryonic | mono-embryonic | poly-embryonic | poly-embryonic |
| Fruit soluble solids | moderate-high | moderate | high | moderate |
| Season of maturity | early-middle | middle | late | early-middle |

-continued

| Character | '11C017R' | 'Ellendale' | 'Murcott' | 'Afourer' |
|---|---|---|---|---|
| Fruit surface texture | smooth | moderate-rough | very smooth | moderate-rough |
| Neck on fruit | absent | slight | absent | slight |
| Ease of peeling | easy | moderate | difficult | easy |
| Fruit firmness | firm | moderate | very firm | moderate-soft |
| Fruit surface (peel) color (RHS) | Orange yellow (RHS 26A) | Orange (RHS 28A) | Orange yellow (RHS 24A) | Orange (RHS 28A) |

-continued

| Character | '11C017R' | 'Ellendale' | 'Murcott' | 'Afourer' |
|---|---|---|---|---|
| Fruit weight (g) | 210 | 190 | 220 | 170 |
| Fruit size | large | large | large | medium |

What is claimed is:

1. A new and distinct mandarin tree called '11C017R' as illustrated and described herein.

* * * * *